United States Patent [19]

Bulten

[11] 4,221,811
[45] Sep. 9, 1980

[54] ANTIFUNGAL AND/OR ANTIBACTERIAL ORGANOTIN COMPOUNDS, AND USE

[75] Inventor: Eric J. Bulten, Bilthoven, Netherlands

[73] Assignee: Nederlandse Centrale Organisatie Voor Toegepast Natuurwetenschappelijk Onderzoek, The Hague, Netherlands

[21] Appl. No.: 870,038

[22] Filed: Jan. 16, 1978

[30] Foreign Application Priority Data

Jan. 17, 1977 [GB] United Kingdom ............... 1779/77

[51] Int. Cl.² ........................... A01N 9/00; C07F 7/22
[52] U.S. Cl. .................... 424/288; 260/429.7
[58] Field of Search ................... 260/429.7; 424/288

[56] References Cited

U.S. PATENT DOCUMENTS

| | | | |
|---|---|---|---|
| 2,236,910 | 4/1971 | Lincoln et al. | 260/429.7 X |
| 3,723,089 | 3/1973 | Peterson | 260/429.7 |
| 3,725,446 | 4/1973 | Peterson | 260/429.7 |
| 3,784,580 | 1/1974 | Peterson | 424/288 X |
| 3,839,052 | 10/1974 | Peterson | 424/288 |
| 3,850,970 | 11/1974 | Peterson et al. | 424/288 X |
| 3,857,942 | 12/1974 | Peterson | 424/288 X |
| 3,976,672 | 8/1976 | Strunk et al. | 424/288 X |

OTHER PUBLICATIONS

J. Organometal Chem. 53, pp. 3 to 5 (1973).
Chemical Reviews, vol. 60 pp. 469-472 (1960).
J. Organometal Chem. 109 pp. 246-251 (1976).
Poller, The Chemistry of Organotin Compounds, Academic Press, N.Y. p. 108 (1970).
Neumann, The Organic Chemistry of Tin, Interscience Publ. N.Y. pp. 90-91 (1970).

*Primary Examiner*—Helen M. S. Sneed
*Attorney, Agent, or Firm*—Brumbaugh, Graves, Donohue & Raymond

[57] ABSTRACT

Antifungal and/or antibacterial organotin compounds characterized by the formula

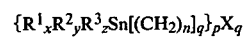

$$\{R^1_x R^2_y R^3_z Sn[(CH_2)_n]_q\}_p X_q$$

in which $R^1$, $R^2$ and $R^3$ represent linear or branched alkyl groups having at most 5 carbon atoms or aryl groups, X represents a functional group linked to a carbon atom, x, y, z, n, p and q are integers, n being 1 to 4 inclusive, p being 1 to 3 inclusive, q being 1 or 2, and if $q=2$ then $x+y+z=2$ and $p=1$ and if $q=1$ then $x+y+z=3$, and methods for preparing said compounds, and methods for using said compounds for controlling fungi and/or bacteria.

3 Claims, No Drawings

ANTIFUNGAL AND/OR ANTIBACTERIAL ORGANOTIN COMPOUNDS, AND USE

The present invention relates to antifungal and/or antibacterial organotin compounds, their preparation and use in compositions having high antifungal and antibacterial activities.

The great majority of organotin compounds—among which the practically important ones—belong to one of the four classes, tetra-, tri-, di-, and monoorganotin compounds, depending on the number of tin carbon bonds:

$$R_4Sn \quad R_3SnY \quad R_2SnY_2 \quad RSnY_3$$

in which R denotes an organic group bound to tin via carbon, and Y stands for any moiety—organic or inorganic—attached to tin via an electronegative atom, e.g. oxygen, nitrogen, sulphur or simply halogen.

It was found in the early 1950's (see "Organometallic Fungicides", chapter 7, in "Fungicides, and Advanced Treatise", vol. II, D. C. Torgeson (ed.), Academic Press, New York, 1969) (1) that many organotin derivatives of the type $R_3SnY$ are powerful fungicides and bactericides. The nature of the organic group R appeared to be of decisive importance in contrast to the nature of the anionic group Y, which does not appreciably influence the activity. Some dialkyltin derivatives $R_2SnY_2$ display interesting antibacterial activity but are inactive against fungi at concentrations $\leq 500$ mg/l.

Monoalkyltin compounds $RSnY_3$ as well as tetraalkyltin compounds $R_4Sn$ do not display antifungal or antibacterial activity at concentrations $\leq 500$ ppm.

In accordance with the above, triorganotin compounds $R_3SnY$, have found large-scale practical application as industrial and agricultural fungicides and bactericides, well-known examples being tributyltin derivatives, $Bu_3SnY$ and triphenyltin derivatives, $Ph_3SnY$ (see citation (1) and "Technische Herstellung und Verwendung von Organozinnverbindungen", A. Bokranz and H. Plum, Topics in Current Chemistry, 16(3/4) (1971) 365-403 (3).

Until recently very little information was available on functionally substituted alkyltin compounds, i.e. compounds bearing one or more functional groups—such as hydroxyl, amine, carboxyl—on one or more carbon atoms of the hydrocarbon chain.

Studies by Noltes, Luijten and Van der Kerk with functionally substituted triorganotin compounds $R_3SnY$ showed that "the introduction of functional substituents in general reduces antifungal activity" (see citation (1) and "The antifungal properties of some functionally substituted organotin compounds", J. Appl. Chem., 11 (1961) 38-40 (4).

It has now been found that, on the one hand, utilizing newly developed synthetic routes disclosed recently (see W.-German patent application No. 2,228,855 (5) and J. Organomet. Chem. 97 (1975) 167 (6a), J. Organomet. Chem. 117 (1976) 329 (6b)), a series of functionally substituted mono-, di-, tri- and tetra-organotin compounds could be synthesized, in which the introduction of functional groups into fungitoxic triorganotin compounds has the effect of abolishing activity rather than increasing it.

On the other hand, it has been found that the introduction of functional groups into hydrocarbon chains can impart high antifungal and/or antibacterial activity to certain classes of organotin compounds.

The present invention comprises antifungal and/or antibacterial organotin compounds, which are characterized by the formula

in which $R^1$, $R^2$ and $R^3$ represent linear or branched alkyl groups having at most 5 carbon atoms or aryl groups, X represents a functional group linked to a carbon atom, x, y, z, n, p and q are integers, n being 1 to 4 inclusive, p being 1 to 3 inclusive, q being 1 or 2, and if q=2 then x+y+z=2 and p=1 and if q=1 then x+y+z=3.

The invention further comprises the preparation of said organotin compounds having the above formula by substituting in a compound having the formula $R_x{}^1R_y{}^2R_z{}^3 Sn(CH_2)_nBr$ the Br atom by a functional group X.

The functional group X is selected from a hydroxyl group, a halogen atom, an ester group, a cyano group, an amino group, an acetamide group, a quaternary ammonium group, a pyridyl group and a piperidine group. Said group X further represents a polyfunctional group such as $-NR^4(CH_2)_n NR^5R^6$, wherein $R^4$, $R^5$ and $R^6$ represent hydrogen, linear or branched alkyl groups, functionally substituted alkyl groups or aryl groups and n represents an integer of 1 to 4 inclusive. Said polyfunctional group is [the dimethylaminopropyl-] preferably amine moiety $-NH(CH_2)_3NMe_2$ or complexes thereof with halogen acids, $-NH-(CH_2)_3NMe_2.2HCl$ or the corresponding quaternary ammonium derivatives, $[-NHR(CH_2)_3NMe_2R]^{2+}$ 2 $Z^-$, R being a linear or branched alkyl group and Z being halogen or other suitable anionic groups.

The invention further provides antifungal and/or antibacterial compositions, which comprise the above defined organotin compounds, as well as a method for preparing said compositions by combining one or more of the said organotin compounds with a suitable carrier. Said carrier is advantageously a solvent and preferably an aqueous solvent.

In the compositions according to the invention also another bactericide or fungicide or insecticide or other active biocidal substances may be taken up. p The invention further provides a process for controlling fungi and/or bacteria, for which purpose one or more of the above defined organotin compounds or compositions respectively are used.

Results obtained are compiled in Tables A and B further below.

For example, the tetraorganotin compound tripropylethyltin is inactive against fungi and bacteria at concentrations $\leq 500$ mg/l.

However, introduction of the 4-pyridyl moiety into the ethyl group imparts high antifungal as well as antibacterial activity to the resulting functionally substituted organotin compound tripropyl-[3-(4-pyridyl)ethyl]tin, $Pr_3SnCH_2CH_2$

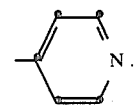

This effect is illustrated once more by the high antifungal activity of tributyl-[3-(4-pyridyl)ethyl]tin, $Bu_3SnCH_2CH_2$

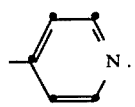

As demonstrated by the data obtained for tributyl-(3-carbomethoxyethyl)tin, $Bu_3SnCH_2CH_2$-COOMe, the introduction of a carboalkoxy group like-wise induces high antifungal and antibacterial activity. The screening data of tributyl(3-bromopropyl)tin, $Bu_3Sn(CH_2)_3Br$, and of tributyl(4-bromopropyl)tin, $Bu_3SN(CH_2)_4Br$, show that bromine substituents are somewhat less effective, although they show a surprisingly effective antifungal activity.

In contrast, the introduction of amino groups and even more so of ammonium moieties can impart strong antifungal and antibacterial activity to tetraorganotin compounds. Thus, tributyl(3-dimethylaminopropyl)tin, $Bu_3Sn(CH_2)_3NMe_2$ and tributyl-(4-dimethylaminobutyl)tin, $Bu_3Sn(CH_2)_4NMe_2$ display strong antifungal activity at concentrations $\leq 20$ mg/l. Both compounds are also very active against gram-positive bacteria ($\sim 3$ mg/l).

As mentioned above, according to the literature the introduction of water-solubilizing substituents in triorganotin compounds has a strongly adverse effect on the antimicrobial activity.

Other examples of this feature were observed during the studies underlying the present invention. For example, triorganotin compounds such as $Bu_3SnBr$, $MeBu_2SnBr$, $MePrBuSnBr$ and the like display strong antifungal activity (1), MIC values being about 10 mg/l. However, introduction of a functional group into one of the alkyl groups of such a triorganotin compound has a detrimental effect on the biocidal activity, viz. antifungal activity of $MeBuBrSn(CH_2)_3NMe_3I$, MIC $>500$ mg/l.

In contrast, the data presented in Tables A and B show that the introduction of such water-solubilizing functional groups in the case of tetraorganotin compounds strongly promotes both antifungal and antibacterial activity.

The nature of the functional substituent is of prime importance with respect to the type of antimicrobial activity induced. For example, introduction of a polyfunctional group such as $-NH(CH_2)_3NR_2$, is of particular advantage in that it imparts broad-spectrum activity, that is high biocidal activity against fungi, Gram-positive bacteria and Gram-negative bacteria.

Several examples given in Table B demonstrate that in this way organotin chemicals can be obtained, which display high MIC values against Gram-negative bacteria such as $E.coli$ and $P.fluorescens$ (3-10 mg/l). These figures compare very favourably with those of the commercially applied tributyltin biocides (100-500 mg/l).

On the basis of the results disclosed in the present invention it can be concluded that those types of organotin compounds that are known to display weak antifungal and antibacterial activity (if any), can be transformed into very active antifungal and antibacterial compounds by incorporating functional substituents, more in particular oxygen and nitrogen containing groups, into the hydrocarbon chain.

The compounds may be used as disinfectants, as agricultural and industrial biocides, in antifouling paints, as preservatives for emulsion paints, in wood-preservation, etc.

The commercially applied triorganotin biocides have several drawbacks, which are mainly caused by the fact that these compounds are virtually insoluble in water. Therefore, these compounds have to be used in organic solvents, which in many cases is considered to be rather unfavourable because of volatility, inflammability or toxicity of these solvents. More in particular for the application of organotin biocides as preservatives for emulsion paints and in wood-preservation, there is an urgent need for organotin biocides having both a high water-solubility and a broad-spectrum activity. In this respect the quite considerable water-solubility of many of the compounds given in Tables A and B is of particular advantage.

For example, the solubility of the commercially applied bis(tributyltin)oxide in water is only 0.003%. In contrast, the solubility in water of $Bu_3Sn(CH_2)_3NMe_2$ is about 2%, whereas the solubility of $[Me_3Sn(CH_2)_2]_2$-

$(CH_2)_3NMe_2.2$ HCl, $MeBu_2Sn(CH_2)_3NH(CH_2)_3$-$NMe_2.2HCl$, $Pr_3Sn(CH_2)_3NH(CH_2)_3NMe_2.2HCl$ and analogous compounds amounts to 50 grams per 100 grams of water, that is 50%.

The synthesis of a number of the compounds in question is illustrated in the following Examples. The identity as well as the purity of the compounds obtained were confirmed by H-NMR spectral analysis, for some compounds after methylation of the compound.

Table A

Antifungal activity of organotin compounds. Minimal concentration (mg/l) causing complete inhibition of visible growth (MIC; after three days).
Test medium: glucose-agar; pH $\sim$ 6.9-7.0.

| Compound | Fungi | | | |
|---|---|---|---|---|
| | Botrytis allii | Penicillium italicum | Aspergillus niger | Cladosporium cucumerinum |
| $Bu_4Sn$ | >500 | >500 | >500 | >500 |
| $Bu_3SnOAc$ | 0.5 | 0.5 | 1 | 1 |
| $Bu_3SnCH_2CN$ | 20 | 5 | 1 | |
| $Ph_3SnCH_2COOSnPh_3$ | $\leq 10$ | $\leq 10$ | $\leq 10$ | |

Table A-continued

Antifungal activity of organotin compounds. Minimal concentration (mg/l) causing complete inhibition of visible growth (MIC; after three days).
Test medium: glucose-agar; pH ~ 6.9–7.0.

| Compound | Fungi | | | |
|---|---|---|---|---|
| | *Botrytis allii* | *Penicillium italicum* | *Aspergillus niger* | *Cladosporium cucumerinum* |
| Pr$_3$SnCH$_2$CH$_2$—(pyridine) | 1 | 2 | 5 | 1 |
| Bu$_3$SnCH$_2$CH$_2$—(pyridine) | 2 | 2 | 50 | ≦1 |
| Bu$_3$Sn(CH$_2$)$_2$CONH$_2$ | ≦10 | ≦10 | ≦20 | ≦10 |
| Bu$_3$Sn(CH$_2$)$_2$COOMe | 0.5 | 1 | 5 | 1 |
| MeBu$_2$Sn(CH$_2$)$_3$Br | 10 | <10 | 100 | <10 |
| MeBu$_2$Sn(CH$_2$)$_3$NH(CH$_2$)$_3$NMe$_2$ | ≦10 | ≦10 | 50 | 50 |
| MeBu$_2$Sn(CH$_2$)$_3$NH(CH$_2$)$_3$NMe$_2$ . 2 HCl | ≦10 | ≦10 | 100 | 20 |
| MePh$_2$Sn(CH$_2$)$_3$NMe$_2$ | 100 | 200 | 500 | 200 |
| MeBuBrSn(CH$_2$)$_3$NMe$_3$I | >500 | >500 | >500 | >500 |
| PrSn(CH$_2$)$_3$Br | 2 | 5 | 2 | 2 |
| Pr$_3$Sn(CH$_2$)$_3$NH(CH$_2$)$_3$NMe$_2$ | ≦10 | ≦10 | 10 | ≦10 |
| Pr$_3$Sn(CH$_2$)$_3$NH(CH$_2$)$_3$NMe$_2$ . 2 HCl | ≦10 | 10 | 20 | 20 |
| Bu$_3$Sn(CH$_2$)$_3$Br | 500 | 500 | 500 | |
| Bu$_3$Sn(CH$_2$)$_3$NMe$_2$ | 10 | 10 | 20 | 20 |
| Bu$_3$Sn(CH$_2$)$_3$NMe$_2$ . HCl | 5 | 5 | 5 | 5 |
| Bu$_3$Sn(CH$_2$)$_3$NMe$_3$I | ≦10 | 50 | 50 | 20 |
| [Bu$_3$Sn(CH$_2$)$_3$NHMe(CH$_2$)$_3$NMe—CH$_2$ / Bu$_3$Sn(CH$_2$)$_3$]$_2$ 4 I$^-$ | ≦10 | ≦10 | 10 | ≦10 |
| Bu$_3$Sn(CH$_2$)$_3$OH | 50 | 100 | 100 | 100 |
| Bu$_3$Sn(CH$_2$)$_3$OCOCH$_3$ | 50 | 20 | 50 | 20 |
| Bu$_2$Sn[(CH$_2$)$_3$NMe$_2$]$_2$ | 50 | 100 | >500 | 500 |
| Bu$_2$Sn[(CH$_2$)$_3$NMe$_3$I]$_2$ | 200 | 200 | >500 | >500 |
| Pent$_3$Sn(CH$_2$)$_3$NMe$_3$I | ≦10 | 20 | 20 | 20 |
| Ph$_3$Sn(CH$_2$)$_3$NMe$_2$ | <10 | <10 | 200 | 50 |
| Ph$_3$Sn(CH$_2$)$_3$NMe$_3$I | 20 | 200 | >500 | 500 |
| Ph$_3$Sn(CH$_2$)$_3$NEt$_2$MeI | 50 | 500 | >1000 | |
| Bu$_3$Sn(CH$_2$)$_3$NH$_2$ | | 2 | 20 | 5 |
| Bu$_3$Sn(CH$_2$)$_4$Br | 500 | 200 | 200 | |
| Bu$_3$Sn(CH$_2$)$_4$NMe$_2$ | ≦10 | 10 | ≦10 | 20 |
| Me$_3$SnCH$_2$CH$_2$ \ / N—(CH$_2$)$_3$NMe$_2$ . 2 HCl / Me$_3$SnCH$_2$CH$_2$ | 2 | 5 | 10 | 5 |

Table B

Antibacterial activity of organotin compounds. Minimal concentration (mg/l) causing complete inhibition of visible growth (MIC; after three days).
Test medium: peptone-glucose agar; pH ~ 6.9–7.0.

| Compound | Gram-pos. bacteria | | Gram-neg. bacteria | |
|---|---|---|---|---|
| | *B. subtilis* | *S. lactis* | *E. coli* | *P. fluorescens* |
| Bu$_4$Sn | >500 | >500 | >500 | >500 |
| Bu$_3$SnOAc | 2 | 5 | >500 | 100 |
| Pr$_3$SnEt | >500 | >500 | >500 | >500 |
| Pr$_3$SnCH$_2$CH$_2$—(pyridine) | 10 | 10 | 100 | 100 |
| Bu$_3$Sn(CH$_2$)$_2$CONH$_2$ | 3 | 10 | >1000 | 300 |
| Bu$_3$Sn(CH$_2$)$_2$COOMe | 30 | 30 | 100 | >1000 |
| MeBu$_2$Sn(CH$_2$)$_3$NH(CH$_2$)$_3$Nme$_2$ | 10 | 10 | 10 | 10 |
| MeBu$_2$Sn(CH$_2$)$_3$NH(CH$_2$)$_3$NMe$_2$ . 2 HCl | 3 | 3 | 3 | 3 |
| MePh$_2$Sn(CH$_2$)$_3$NMe$_2$ | 100 | 100 | 1000 | 1000 |
| Ph$_3$Sn(CH$_2$)$_3$Br | 300 | 1000 | >1000 | >1000 |
| Pr$_3$Sn(CH$_2$)$_3$NH(CH$_2$)$_3$NMe$_2$ | 10 | 10 | 10 | 10 |
| Pr$_3$Sn(CH$_2$)$_3$NH(CH$_2$)$_3$NMe$_2$ . 2 HCl | 10 | 10 | 10 | 10 |
| Bu$_3$Sn(CH$_2$)$_3$NMe$_2$ | 3 | 3 | 300 | 1000 |
| Bu$_3$Sn(CH$_2$)$_3$NMe$_2$ . HCl | 10 | 10 | 300 | 300 |
| Bu$_3$Sn(CH$_2$)$_3$NMe$_3$I | ≦1 | ≦1 | 30 | 300 |

Table B-continued

Antibacterial activity of organotin compounds. Minimal concentration (mg/l) causing complete inhibition of visible growth (MIC; after three days). Test medium: peptone-glucose agar; pH ~ 6.9–7.0.

| Compound | Gram-pos. bacteria | | Gram-neg. bacteria | |
|---|---|---|---|---|
| | B. subtilis | S. lactis | E. coli | P. fluorescens |
| $[Bu_3Sn(CH_2)_3NHMe(CH_2)_3NMe-CH_2\underset{Bu_3Sn(CH_2)_3}{|}]^{4+} 4I^-$ | 30 | 100 | 1000 | 1000 |
| $Bu_3Sn(CH_2)_3OH$ | 1000 | 300 | >1000 | >1000 |
| $Bu_3Sn(CH_2)_3OCOCH_3$ | 100 | 100 | >1000 | 300 |
| $Bu_3Sn(CH_2)_3Br$ | 300 | 300 | >1000 | >1000 |
| $Bu_2Sn[(CH_2)_3NMe_2]_2$ | 100 | 100 | 100 | 300 |
| $Bu_2Sn[(CH_2)_3NMe_3I]_2$ | 300 | 300 | >1000 | >1000 |
| $Ph_3Sn(CH_2)_3NMe_2$ | 10 | 10 | 300 | >1000 |
| $Ph_3Sn(CH_2)_3NMe_3I$ | 10 | 10 | 1000 | 1000 |
| $Bu_3Sn(CH_2)_4NH_2$ | 3 | 3 | 300 | 300 |
| $Bu_3Sn(CH_2)_4NMe_2$ | 3 | 3 | >300 | >300 |
| $Me_3SnCH_2CH_2$  $\diagdown$  N—$(CH_2)_3NMe_2$ · 2 HCl  $Me_3SnCH_2CH_2$  $\diagup$ | 10 | 10 | 30 | 300 |

The antifungal and antibacterial compositions according to the present invention may contain another bactericide or fungicide or insecticide or other active biocidal substances.

EXAMPLE I (A) The preparation of $Br_3Sn(CH_2)_nBr$ (n = 3–4)

A mixture of 111.6 g (0.40 mol) of anhydrous $SnBr_2$, 363 g (1.80 mol) of $Br(CH_2)_3Br$ and 4 ml (5.25 g, 0.025 mol) of $Et_3Sb$ was stirred for 4.5 h at 150°–160° C. The $SnBr_2$ had been completely converted. Evaporation in vacuo (14 mm Hg) at 100° C. gave 272 g (1.35 mol) of recovered $Br(CH_2)_3Br$, leaving 206 g of a brown, oily liquid. Distillation in vacuo (mercury diffusion pump) gave 141.6 g (74%) of pure $Br_3Sn(CH_2)_3Br$. In a similar way $Br_3Sn(CH_2)_4Br$ was prepared.

(B) The preparation of $R_3Sn(CH_2)_nBr$ (n = 3–4)

A solution of 20 g (0.042 mol) of $Br_3Sn(CH_2)_3Br$ in 100 ml of diethyl ether was added drop-wise to 80 ml of a 2.5 N solution of MeMgBr in diethyl ether. After reflux for 2 h the mixture was treated with a saturated aqueous solution of $NH_4Cl$ and distilled to give 8.7 g (74%) of (3-bromopropyl)trimethyltin.

In a similar way were prepared: (3-bromopropyl)tripropyltin, (3-bromopropyl)tributyltin, (3-bromopropyl)tripentyltin and (3-bromopropyl)triphenyltin, (4-bromobutyl)tributyltin and related compounds.

(C) The preparation of $R_x^1R_y^2R_z^3Sn(CH_2)_nBr$ (n = 3, 4)

Over a period of 1.5 hour 140 g (0.874 mol) of bromine was added to a solution of 125 g (0.437 mol) of $Me_3Sn(CH_2)_3Br$ in 450 ml of methanol kept at −20° C. The mixture was stirred at room temperature till the orange-red colour had changed into slightly yellow. Evaporation of the solvent in vacuo gave 174 g (96%) of (3-bromopropyl) methyltin dibromide, $n_D^{20} = 1.6215$.

A solution of 115 ml of 2.7 N butylmagnesium bromide in diethyl ether was added in about one hour to a solution of 62.5 g (0.15 mol) of (3-bromopropyl)methyltin dibromide in 200 ml of diethyl ether. After reflux for 1 h the mixture was treated with a saturated aqueous solution of $NH_4Cl$ and distilled to give 48.79 g (88%) of (3-bromopropyl)methyldibutyltin; b.p. 88°–90° C./0.1 mm Hg, $n_D^{20} = 1.5001$.

In a similar way were prepared (3-bromopropyl)methyldiphenyltin and related compounds.

EXAMPLE II

The preparation of $Bu_3Sn(CH_2)_3NMe_2$ and related compounds

In a reaction vessel provided with a carbon dioxide condenser, a mixture of 6.18 g (0.015 mol) of $Bu_3Sn(CH_2)_3Br$ and 20 ml of $Me_2NH$ was refluxed for 7 h. The residue obtained after evaporation of the excess of $Me_2NH$ was taken up in 30 ml of diethyl ether and treated for 15 min with 50 ml of a 10% aqueous solution of $NaHCO_3$. Distillation gave 4.95 g (86%) of (3-dimethylaminopropyl)tributyltin.

Analogously were prepared: (3-dimethylaminopropyl) methyldiphenyltin, (3-dimethylaminopropyl)trimethyltin, (3-dimethylaminopropyl)triphenyltin, (4-dimethylaminobutyl)tributyltin and related compounds.

EXAMPLE III

The preparation of N-[3-(tripropylstannyl)propyl-N', N'-dimethyltrimethylene]diamine, $Pr_3Sn(CH_2)_3NH(CH_2)_3NMe_2$ Over a period of 0.5 hour 9.25 g (0.025 mol) of (3-bromopropyl) tripropyltin was added to 25 ml of 3-dimethylaminopropyl amine at room temperature. The mixture was stirred for 1 hour at 60° C. Under cooling 75 ml of diethylether and 60 ml of a 15% aqueous solution of sodium bicarbonate were added. After stirring for 0.5 hour the organic phase was separated, dried and evaporated in vacuo. Distillation gave 7.5 g (77%) of $Pr_3Sn(CH_2)_3NH(CH_2)_3NMe_2$; b.p. 113°–114° C./0.1 mm Hg, $n_D^{20} = 1.4855$.

In a similar way were prepared N-[3-(methyldibutylstannyl) propyl-N', N'-dimethyltrimethylene]diamine, $MeBu_2Sn(CH_2)_3NH(CH_2)_3NMe_2$, $\{Bu_3Sn(CH_2)_3NH(CH_2)_3N[(CH_2)_3SnBu_3]CH_2\}_2$ and related compounds.

By conventional techniques the products can be readily converted into the corresponding halogen acid salts, quaternary ammonium derivatives, and the like.

EXAMPLE IV

Bis(trimethylammoniopropyl)dibutyltin diiodide, $Bu_2Sn[(CH_2)_3NMe_3I]_2$

A solution of 22.8 g (0.075 mol) of $Bu_2SnCl_2$ in 80 ml of benzene was added slowly at 0° C. to 70 ml of a TMF solution containing 0.18 mol of (3-dimethylaminopropyl)magnesium chloride. The resulting mixture was diluted with 100 ml of diethyl ether and refluxed for 2 hours. After the usual work-up the product was distilled to give 28.1 g (92.5%) of $Bu_2Sn[(CH_2)_3NMe_2]_2$; b.p. 112°–114° C./0.0 mm Hg, $n_D^{20} = 1.4829$.

To a solution of 6.1 g (0.015 mol) of $Bu_2Sn[(CH_2)_3NMe_2]_2$ in 50 ml of methanol was added slowly 4.26 g (0.03 mol) of methyl iodide. Evaporation in vacuo gave 10.2 g (97%) of solid $Bu_2Sn[(CH_2)_3NMe_3I]_2$; m.p. 194°–195° C.

What we claim is:

1. An organotin compound having the formula:

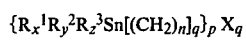

$$\{R_x^1 R_y^2 R_z^3 Sn[(CH_2)_n]_q\}_p X_q$$

wherein $R^1$, $R^2$ and $R^3$ are linear or branched alkyl groups having at most five (5) carbon atoms or aryl groups, X is a functional group linked to a carbon atom and selected from the group consisting of:

(a) $-NR^4(CH_2)nNR^5R^6$, wherein $R^4$, $R^5$ and $R^6$ are hydrogen, linear or branched alkyl groups or aryl groups and n is an integer from 1 to 4 inclusive; and (b) dimethylaminopropylamine moiety, $-NH(CH_2)_3-NMe_2-$ and complexes thereof with halogen acids, $-NH-(CH_2)_3-NMe_2.2HCl$, or corresponding quarternary ammonium derivatives, $[-NHR(CH_2)_3-NMe_2R]^{2+}2Z^-$ wherein R is a linear or branched alkyl group and Z is halogen or another suitable anionic group; and x,y,z, n, p and q are integers, n being 1 to 4 inclusive, p being 1 to 3 inclusive, q being 1 or 2, and if q equals 2 then x+y+z equals 2 and p equals 1 and if q equals 1 then x+y+z equals 3.

2. An antifungal and (or) antibacterial composition comprising as an active ingredient at least one compound according to claim 1 in an amount effective to impart antifungal and (or) antibacterial properties, and in combination with a suitable solid or liquid carrier.

3. A process for controlling fungi and (or) bacteria comprising contacting said fungi and (or) bacteria with a compound according to claim 1, in an amount effective for the control of the fungi and (or) bacteria.

* * * * *

UNITED STATES PATENT AND TRADEMARK OFFICE
CERTIFICATE OF CORRECTION

PATENT NO. : 4,221,811

DATED : September 9, 1980

INVENTOR(S) : Eric J. Bulten

It is certified that error appears in the above-identified patent and that said Letters Patent are hereby corrected as shown below:

Column 2, Line 7, that part of the formula reading "$R_x^1 R_y^2 R_z^3$" should read --$R^1_x R^2_y R^3_z$--;

Column 2, Line 20, "$R_x^1 R_y^2 R_z^3$" should read --$R^1_x R^2_y R^3_z$--;

Column 2, Line 47, delete "p";

Column 2, Lines 47-48, "The invention..." should start a new paragraph;

Column 5, Table A-continued, 17th item under heading "Compound", closing bracket should be extended up alongside "4+";

Column 5, Table B, 7th item under heading "Compound", "$Nme_2$" should read --$NMe_2$--;

UNITED STATES PATENT AND TRADEMARK OFFICE
CERTIFICATE OF CORRECTION

PATENT NO. : 4,221,811
DATED : September 9, 1980
INVENTOR(S) : Eric J. Bulten

It is certified that error appears in the above-identified patent and that said Letters Patent are hereby corrected as shown below:

Column 7, Line 55, "$R_x{}^1 R_y{}^2 R_z{}^3$" should read --$R^1{}_x R^2{}_y R^3{}_z$--; and Column 9, Line 22, "$R_x{}^1 R_y{}^2 R_z{}^3$" should read --$R^1{}_x R^2{}_y R^3{}_z$--.

Signed and Sealed this

*Twenty-fourth* Day of *February 1981*

[SEAL]

*Attest:*

RENE D. TEGTMEYER

*Attesting Officer*     *Acting Commissioner of Patents and Trademarks*